(12) United States Patent
Laufer

(10) Patent No.: US 8,909,347 B2
(45) Date of Patent: *Dec. 9, 2014

(54) LOCATION AND DEACTIVATION OF MUSCLES

(71) Applicant: Michael D. Laufer, Menlo Park, CA (US)

(72) Inventor: Michael D. Laufer, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,989

(22) Filed: Jul. 24, 2013

(65) Prior Publication Data

US 2014/0058285 A1    Feb. 27, 2014

Related U.S. Application Data

(63) Continuation of application No. 11/743,121, filed on May 1, 2007, now Pat. No. 8,521,295, which is a continuation-in-part of application No. 11/234,547, filed on Sep. 23, 2005, now abandoned.

(60) Provisional application No. 60/796,688, filed on May 1, 2006, provisional application No. 60/612,385, filed on Sep. 23, 2004.

(51) Int. Cl.
| | |
|---|---|
| *A61N 1/18* | (2006.01) |
| *A61B 5/04* | (2006.01) |
| *A61B 18/14* | (2006.01) |
| *A61N 7/02* | (2006.01) |
| *A61N 1/05* | (2006.01) |
| *A61B 5/00* | (2006.01) |
| *A61B 18/00* | (2006.01) |
| *A61N 1/32* | (2006.01) |

(52) U.S. Cl.
CPC ............. *A61B 5/04001* (2013.01); *A61B 18/14* (2013.01); *A61N 7/02* (2013.01); *A61N 1/0551* (2013.01); *A61B 5/4893* (2013.01); *A61B 2018/00434* (2013.01); *A61N 1/328* (2013.01)
USPC ........................................................ 607/48

(58) Field of Classification Search
None
See application file for complete search history.

(56) References Cited

U.S. PATENT DOCUMENTS

| 4,057,069 A | 11/1977 | Dorffer et al. |
| 4,084,595 A | 4/1978 | Miller |

(Continued)

OTHER PUBLICATIONS

Hernandez-Zendejas, Gregorio et al, "Percutaneous Selective Radio-Frequency Neuroablation in Plastic Surgery," *Aesth. Plast. Surg.*, 18:41-48, 1994.

*Primary Examiner* — Brian T Gedeon
(74) *Attorney, Agent, or Firm* — Levine Bagade Han LLP

(57) ABSTRACT

Methods and devices for treatment to at least interfere with the function of a muscle are described herein. These methods and devices may have application in cosmetic and plastic surgery, dermatology, suppression of tension and/or migraine-type headaches, pain management, one particular application of the subject matter deals primarily with reducing wrinkles caused by ongoing muscular activation. The devices and methods described herein allow medical practitioners to effectively identify selective nerves for paralyzing muscles, without the need for injections of agents such as botulism toxin. Moreover, the devices and methods herein, may allow for artificial generation of signals in nerves that were otherwise damaged by stimulating transmission of nerve signals across damaged nerves.

13 Claims, 6 Drawing Sheets

(56) References Cited

U.S. PATENT DOCUMENTS

| | | |
|---|---|---|
| 4,232,680 A | 11/1980 | Hudleson et al. |
| 4,284,856 A | 8/1981 | Hochmair et al. |
| 4,535,777 A | 8/1985 | Castel |
| 4,712,558 A | 12/1987 | Kidd et al. |
| 4,957,480 A | 9/1990 | Morenings |
| 4,962,766 A | 10/1990 | Herzon |
| 5,284,153 A | 2/1994 | Raymond et al. |
| 5,284,154 A | 2/1994 | Raymond et al. |
| 5,476,438 A | 12/1995 | Edrich et al. |
| 5,690,681 A * | 11/1997 | Geddes et al. ............ 607/2 |
| 5,690,981 A | 11/1997 | Watanabe et al. |
| 5,766,124 A | 6/1998 | Polson |
| 5,891,185 A | 4/1999 | Freed et al. |
| 6,066,084 A | 5/2000 | Edrich et al. |
| 6,139,545 A | 10/2000 | Utley et al. |
| 6,312,392 B1 | 11/2001 | Herzon |
| 6,393,323 B1 | 5/2002 | Sawan et al. |
| 6,662,051 B1 | 12/2003 | Eraker et al. |
| 6,701,185 B2 | 3/2004 | Burnett et al. |
| 6,885,888 B2 | 4/2005 | Rezai |
| 7,454,245 B2 | 11/2008 | Armstrong |
| 2005/0182454 A1 | 8/2005 | Gharib et al. |
| 2006/0167500 A1 | 7/2006 | Towe et al. |
| 2007/0255342 A1 | 11/2007 | Laufer |

\* cited by examiner

LOCATION AND DEACTIVATION OF MUSCLES

CROSS REFERENCE TO RELATED APPLICATIONS

This application is a continuation of U.S. patent application Ser. No. 11/743,121 entitled "LOCATION AND DEACTIVATION OF MUSCLES" filed on May 1, 2007, which is a continuation in part of U.S. patent application Ser. No. 11/234,547 entitled "LOCATION AND DEACTIVATION OF MUSCLES" filed Sep. 23, 2005, now abandoned, which is a non-provisional of U.S. provisional application No. 60/612,385 entitled "LOCATION AND DEACTIVATION OF MUSCLES" filed Sep. 23, 2004; this is also a non-provisional of U.S. provisional application No. 60/796,688 entitled "LOCATION AND DEACTIVATION OF MUSCLES" filed May 1, 2006, the entirety of each of the above is incorporated by reference.

BACKGROUND

Devices and methods using energy to stimulate nerves in the body is well known. Such methods and devices are discussed in U.S. Pat. No. 4,712,558, titled ELECTRICAL STIMULATION OF MUSCLE, issued Dec. 15, 1987; U.S. Pat. No. 4,957,480, titled METHOD OF FACIAL TONING, issued Sep. 18, 1990; U.S. Pat. No. 4,962,766 titled NERVE LOCATOR AND STIMULATOR, issued Oct. 16, 1990; U.S. Pat. No. 5,284,153 titled METHOD FOR LOCATING A NERVE AND FOR PROTECTING NERVES FROM INJURY DURING SURGERY, issued Feb. 8, 1994; U.S. Pat. No. 5,284,154 titled APPARATUS FOR LOCATING A NERVE AND FOR PROTECTING NERVES FROM INJURY DURING SURGERY, issued Feb. 8, 1994; U.S. Pat. No. 5,476,438, titled METHOD AND APPARATUS FOR NEUROMAGNETIC STIMULATION, issued Dec. 19, 1995; U.S. Pat. No. 5,766,124, titled MAGNETIC STIMULATOR FOR NEURO-MUSCULAR TISSUE, issued Jun. 16, 1998; U.S. Pat. No. 6,066,084, titled METHOD AND APPARATUS FOR FOCUSED NEUROMAGNETIC STIMULATION AND DETECTION, issued May 23, 2000; and U.S. Pat. No. 6,701,185, titled METHOD AND APPARATUS FOR ELECTROMAGNETIC STIMULATION OF NERVE, MUSCLE, AND BODY TISSUES, issued Mar. 2, 2004; the entirety of each of which is incorporated by reference herein. It is contemplated that features of the references discussed above may be incorporated into the devices described herein, In addition, the desire to deactivate certain muscles has gained popularity following the clinical use of Botulinum Toxin Type A in cosmetic procedures.

In early 2000, medical practitioners observed that Botulinum Toxin Type A softened the vertical frown (glabellar) lines between the eyebrows (where such frown lines tend to make people look tired, angry or displeased.) Eventually, the U.S. FDA permitted use of the drug for the condition of reducing the severity of frown lines for up to 120 days.

Botulinum Toxin Type A is a protein complex produced by the bacterium *Clostridium botulinum*. This toxin is the same that causes food poisoning. However, when used in a medical procedure, the toxin is in an injectable form of sterile, purified botulinum toxin. Small injected doses of the toxin block the release of a chemical called acetylcholine by nerve cells that signal muscle contraction. The goal of the procedure is to use the toxin to selectively interfere with the underlying muscles' ability to contract. The effect is that existing frown lines smooth and are reported to become nearly invisible on a temporary basis.

While it is believed that there is no chance of contracting botulism from such injections, there are risks associated with the procedure. For example, too much toxin may be injected by those inexperienced in the procedure or the toxin may be injected into the wrong facial area causing an undesired treatment effect, Other reported side-effects include headache, respiratory infection, flu syndrome, and nausea. Less frequent adverse reactions included pain in the face, redness at the injection site, and muscle weakness. These reactions were generally temporary, but could last several months.

The apparent success of Botulinum Toxin Type A use in cosmetic procedures demonstrates the demand for non-invasive cosmetic procedures. However, as noted above, there are drawbacks to such procedures that may be overcome. For example, eliminating the use of the toxin may serve to reduce the side-effects caused by the substance. Moreover, if the medical practitioner could test the intended target area prior treatment, undesired treatment effects may be avoided or reduced, in view of the above there remains a need for devices and methods that may eliminate some of the side-effects or risks of the cosmetic procedure discussed above,

SUMMARY OF THE INVENTION

Various examples of the invention are described below, Such examples are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Moreover, it is intended that the disclosure includes various combinations of the examples or even certain aspects of the examples where such combinations are possible.

The methods and devices disclosed herein enable location and deactivation of muscles and their associated nerves, Although the variations disclosed discuss applications with cosmetic surgery, the subject invention may be incorporated in various other medical areas as well.

The methods disclosed herein further provide a non-invasive method for testing nerve and muscle function, eliminating the need for electrode needle insertion for nerve stimulation, and providing finer resolution to the assessment of function. Seizure foci can also be discovered and treated with the methods and devices disclosed herein.

BRIEF DESCRIPTION OF THE DRAWINGS

The figures shown herein are not necessarily drawn to scale, with some components and features being exaggerated for clarity. Each of the Figures diagrammatically illustrates aspects of the invention. Of these.

DETAILED DESCRIPTION OF THE INVENTION

In general, this invention includes locating a site to treat a neuro-muscular complex to at least interfere with the function of a muscle. While the invention includes many variations and application, including, but not limited to, cosmetic and plastic surgery, dermatology, suppression of tension and/or migraine-type headaches, pain management, one particular application of the invention deals primarily with reducing wrinkles caused by ongoing muscular activation. Specifically, this is of interest in the fields of plastic surgery and dermatology. The invention described herein allows the skilled practitioner to effectively paralyze muscles, especially in the face and head, without the need for injections of agents such as botulism toxin. One notable benefit of the inventive treatment described herein is also longer lasting and potentially permanent effect, as opposed to injections that are transient, lasting about 3-6 months. Additional significant advantages include added persistence of effect and an increase in effectiveness while being non-invasive. In addition, partial paralysis can be attained and the effect can be reproducibly attained.

A variation of the invention includes locating a site for treatment of a neuromuscular complex through the stimulation of a nerve which normally triggers the muscle, then directing energy at or through the nerve to prevent the nerve (and as a result the muscle) from properly functioning. It follows that one variation of a device for use in the present invention includes a device that allows the practitioner to non-invasively locate muscles and then stimulate the associated nerves in a safe manner. The device also, allows the medical practitioner to accurately target the muscle and/or nerve, and then allows directing of energy into the targeted structure to prevent it from subsequently functioning. The device and method can also be used to target sensory nerves in order to alleviate pain and/or undesirable sensations. It can also be used to locate nerves so as to avoid them during subsequent procedures that might cause them unintentional injury.

Figure 1:
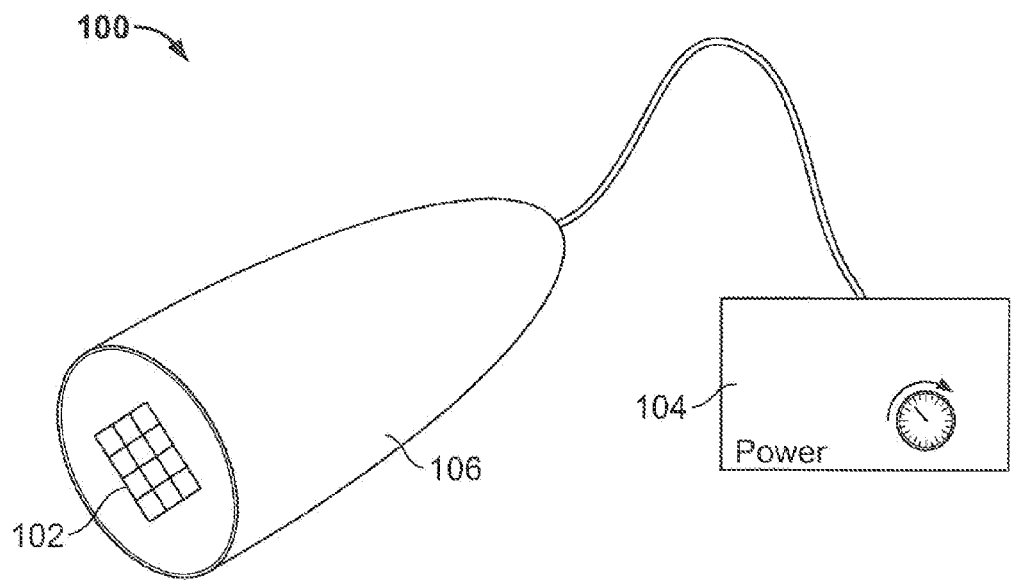
FIG. 1 shows a system for use in the present invention as having an array of transducers.
Figure 2:
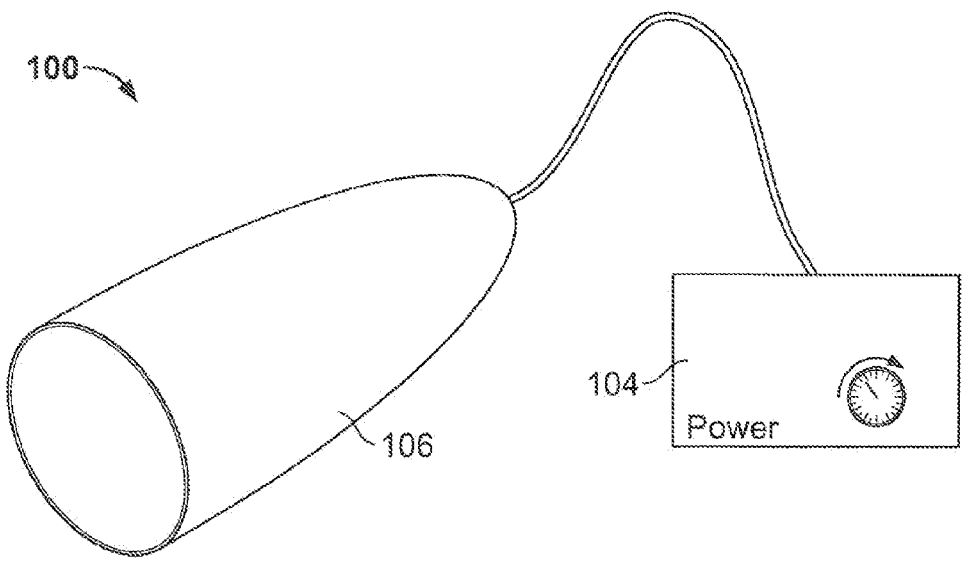
FIG. 2 shows a system under the present invention.

One example of a device 100 for use in the present invention is as shown in FIGS. 1 and 2. An array of ultrasonic transducers 102 is arranged to provide a focal point that is variable from the expected thickness of the skin of 1 mm from the surface of the transducer, to 5 mm into the depth of the skin. However, the depth may be greater as required for the particular indication. The transducers are connected to a power source 104 that is variable. At low power, the ultrasound, if focused on a nerve, will be sufficient to cause nerve stimulation and muscular activation. When used under a low power, the practitioner will see twitching of the targeted muscle upon location of the nerve. When the target muscle to be inactivated begins twitching, the operator increases the power to the transducers. At this setting, the focused ultrasound damages the target tissue. In this example, the target tissue will typically be the nerve supplying the muscle targeted for inactivation. To test the procedure, the muscle may be stimulated by either voluntary or artificial means. The inability to cause muscle movement with further stimulation subsequently, either by voluntary muscle activation or by electronic stimulation, demonstrates achievement of the desired effect. Other muscles and nerves can be subsequently targeted and inactivated and/or paralyzed. Naturally, the ultrasound transducers 102 may be carried in a housing 106 where such a structure includes a housing, handle, catheter, or other structure as commonly used in medical appliances.

This treatment is longer lasting and potentially permanent due to the fact that the damaged nerve requires Wallerian degeneration and regeneration before the muscle would work again. This process takes, on the order of, one year or so if it takes place at all. Furthermore, while current treatments, such as botulism toxin injections, wear off without any sustained benefit, inactivation of the nerve will, over time, also cause the muscle to atrophy. Therefore, with this novel treatment, even if the nerve regenerates, after several treatments, the regeneration of the nerve may be inconsequential because the muscle has atrophied and can no longer function even if stimulated by the nerve.

Figure 3A:
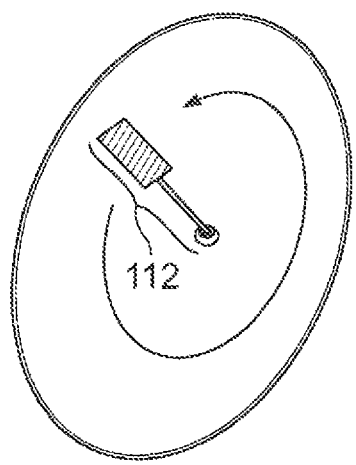
FIGS. 3A and 3B illustrate a variation of a system having a single moving transducer forming a virtual array.
Figure 3B:
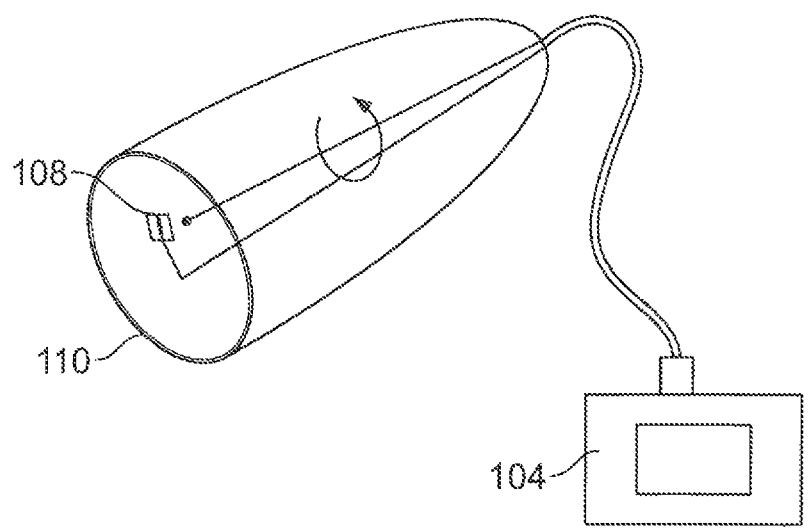

As shown in FIGS. 3A and 3B, additional configurations of the device replace the array of transducers with a moving single transducer 108 representing a virtual array. Of course, multiple moving transducers could also be used. The transducer(s) 108 are mounted on a moving, or rotating, member 110. As the transducer is moved, the field of ultrasound becomes bi-conical. The apex of the cones becomes the focal point of energy. By changing the angle of incidence of the ultrasound with the skin surface, the depth of the focal point can be altered. This angular change can be accomplished by either changing the radius of rotation or movement of the transducer 112, or by changing the angle at which the transducers send energy with respect to the skin and device as shown. Both the radius and angle can also be changed. In this way, the depth of the focal point can be altered as well as the size of the focal point.

Alternatively, passing small amounts of current through an area where the nerve is thought to be located can also identify the nerve, When twitching occurs, a brief, high-voltage current is passed through the same area. Because the relative impedance of the nerve is lower than that of the surrounding tissue, more current will pass through the nerve. As a result, the nerve will heat and will become damaged. Radiofrequency energy also is one of several modes useful to cause this injury. Again, as discussed above, the damage may be permanent or at least long lasting. Of course any and all of these modalities can be used in combination, such as electrical stimulation for locating the target and ultrasound focused on the area so stimulated for damaging the nerve.

The method of use consists of locating the area to be treated, treating the area and testing to assure complete treatment was achieved. Locating the target is accomplished by using low levels of power to limit damage. An acoustic coupling medium is applied between the transducer and skin. With the virtual array, the depth of the focal point is varied simultaneously with moving the transducer over the skin. When muscular movement is detected, the virtual array unit is held in position and the angle of the transducers is changed until muscle response is maximized. Once this occurs (and the depth of the focal point is thereby also established), the power is increased and the nerve is destroyed. With any of the devices, then, the device is properly positioned and the energy focused to maximize the muscular response to the stimulation from the device, the power is increased and the target is damaged. The patient is then asked to furrow their brow, for instance. If there is no movement in the targeted muscles, it is determined that the procedure was successfully completed. The procedures can be repeated until the desired level of paralysis is obtained. The muscle can also be targeted. Abnormal tissues can also be targeted such as neuromata and vascular masses, such as strawberry birthmarks.

Figure 4:
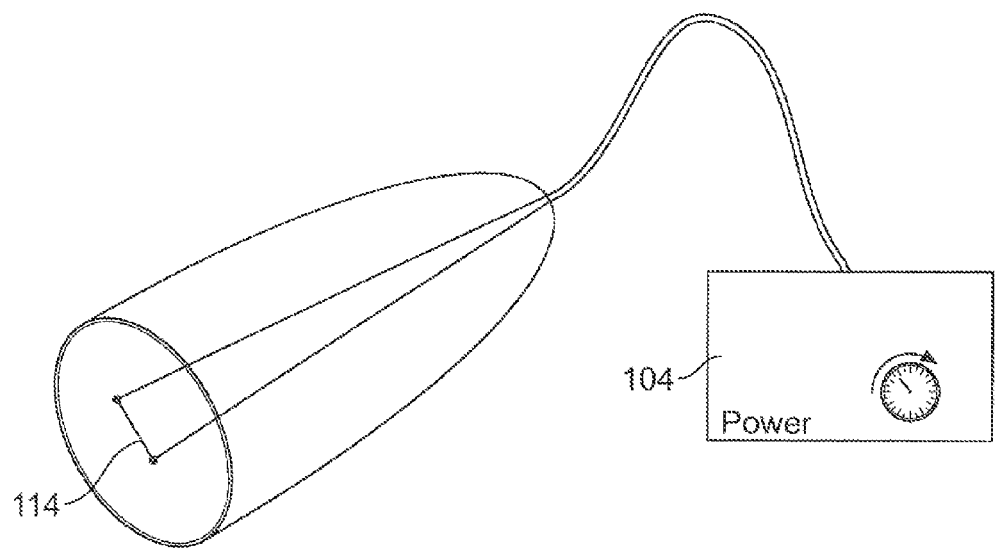
FIG. 4 illustrates a variation of the system having a wire.
Figure 5:
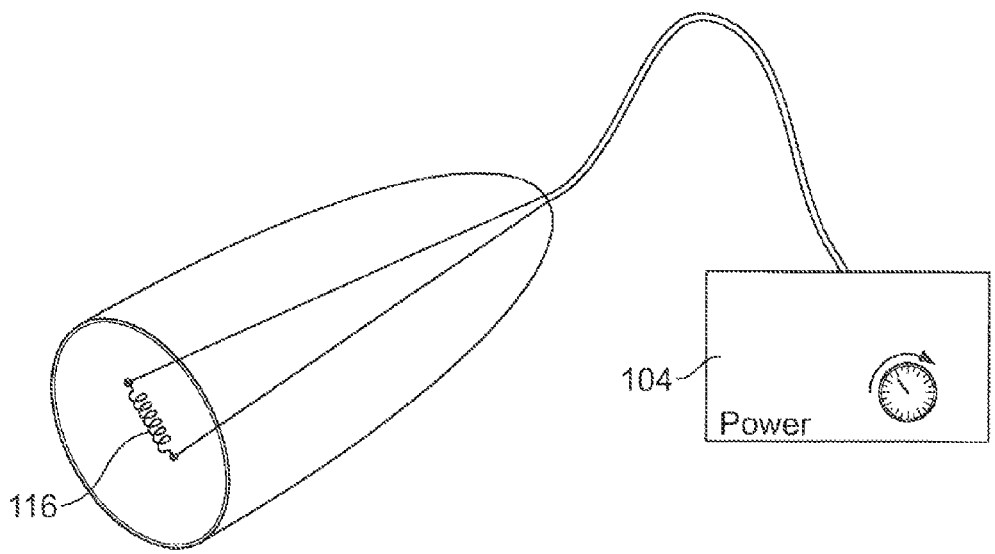
FIG. 5 illustrates a variation of the system that uses a coil to transfer energy.

FIG. 4 shows another localization/destruction device and method. For example, a high-voltage (20,000 Volts) low current (1-100 milliamps) alternating current is passed through a wire 114 that is between one and 10 mm long in its straight testing portion as shown. The current is measured. As the energized wire is passed over the skin and turned as shown, the current will drop as the wire induces a voltage and current flow in a nerve with which it is electrically coupled. The muscle is stimulated, providing confirmation of appropriate positioning. The current drop will be maximized when the wire and the nerve are parallel and in maximal proximity. At the position of maximal current drop, the voltage and/or current are increased to induce a larger current in the nerve. This will cause heating and damage to the nerve, which will in turn result in muscular paralysis. The procedure can be repeated until no additional muscle activity is seen. It can then be repeated for other neuromuscular complexes where the effect of paralysis is desired. As illustrated in FIG. 5, a coil 116 can also be used in place of a single straight wire if a greater current boost is desired. Alternatively, the aforementioned device can be used for localization, at which point another destructive device as previously described can be used to destroy the neuromuscular complex. It is noted that additional variations of the invention include the use of two or more wires or coils in the variations shown herein.

Figure 6:
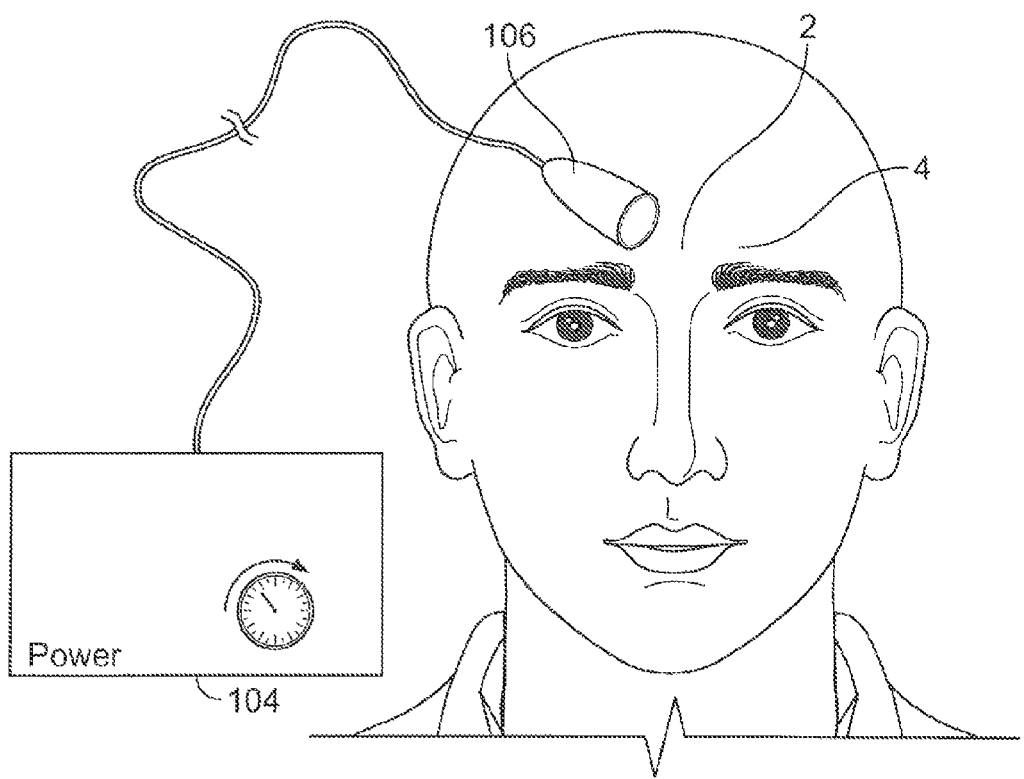
FIG. 6 illustrates a variation of the system when used in a facial procedure.

In a general sense the procedure includes a method of treating a muscle comprising applying a first amount of energy to tissue where the first amount of energy is sufficient to stimulate a nerve, and applying a second amount of energy upon observation of stimulation of the muscle that is triggered by the stimulation of the nerve, where the second amount energy is sufficient to impair the nerve (e.g., motor fibers, sensory fibers, and/or pain fibers). In the procedure described immediately above, the tissue may comprise facial tissue, the muscle may comprise the corrugator and/or procerus muscles. For example, as shown in FIG. 6, the device housing 106 may be placed over the desired area of treatment (e.g., the region of the procerus muscle 2 or the region of the corrugator muscle 4). The medical practitioner may then attempt to stimulate the nerve and observe movement of the region/muscle. Once the region is identified, the energy is increased to sufficiently impair the nerve.

It is, of course, also contemplated that chronic pain syndromes can be treated by moving the device over an area until pain is reproduced, at which point the energy is increased and the nerve responsible for conducting the pan sensation, is damaged. This reduces the pain.

A variation of the methods and devices also allow for bypass of damaged nerves. Nerves function in a circuit-type fashion. A signal transmits back and forth between the nerve and brain through the nerve circuit. Damaged nerves breaks the circuit preventing a signal from traveling to nerves across the damaged site. The methods and devices described herein allow selective stimulation of the nerves below the damaged site to mimic the observed signal coming from nerves above the damaged site. Transmitting the signal around damaged nerves is especially useful in spinal nerve injury or in peripheral nerve injury. Selective stimulation of nerves in an otherwise damaged circuit also allows for stimulation of muscles. The devices and methods described herein allow signals in the nerve's circuit to bypass the damaged nerve and stimulate the intended nerves. For example, in one variation, in cases where the nerve circuit is damaged a sensing circuit device identifies a signal that is transmitted along the nerve. The sensing circuit then communicates with a stimulating circuit device to stimulate the muscles or nerves across the damaged site. The stimulatng circuit device could also be used to perform electromyography (EMG) stimulation with or without the currently required needles.

Figure 7:
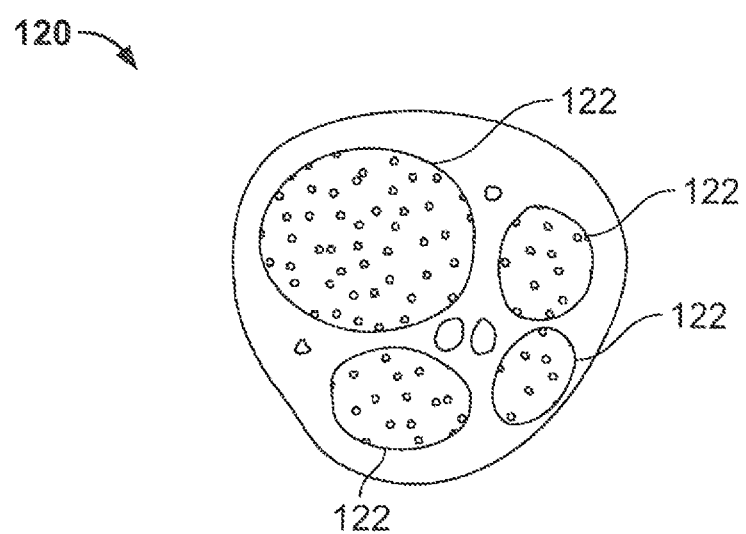
FIG. 7 illustrates a cross-sectional view of a nerve bundle.

FIG. 7 illustrates a cross-sectional view of a nerve bundle 120. The nerve bundle 120 consists of a number of nerve strands 122 Where some nerve strands (axons) are surrounded by a myelin sheath that facilitates the transmission of the nerve signal. The axon at rest has a fixed capacitance C and fixed resistance R. It The resistance is a function of the linear membrane characteristics of the axon while the capacitance is a function of the membrane's separation of charges from inside to outside of the cell. Each nerve strand 122 has a characteristic C and R, explaining why signals in adjacent nerve strands 122 do not interfere with each other or cross. it is believed that the product of R and C (RC) creates a primary resonance frequency similar to that in a radio receiver. By discovering the particular frequency for a nerve strand 122 and then applying stimulation at that particular frequency or at an integral multiple of it (i.e. a harmonic frequency), the nerve strand 122 can be stimulated selectively, The effect of this stimulation can be detected by amplifying the nerve action potential, by detecting muscle activity in correlation with the stimulation or by similar methods such as patient reporting of sensation or movement. The primary frequency of motor nerves is believed to be in the range of 30 Hz-500 Hz. However, depending on harmonics the range may go higher (e.g., 2 KHz.).

Figure 8:
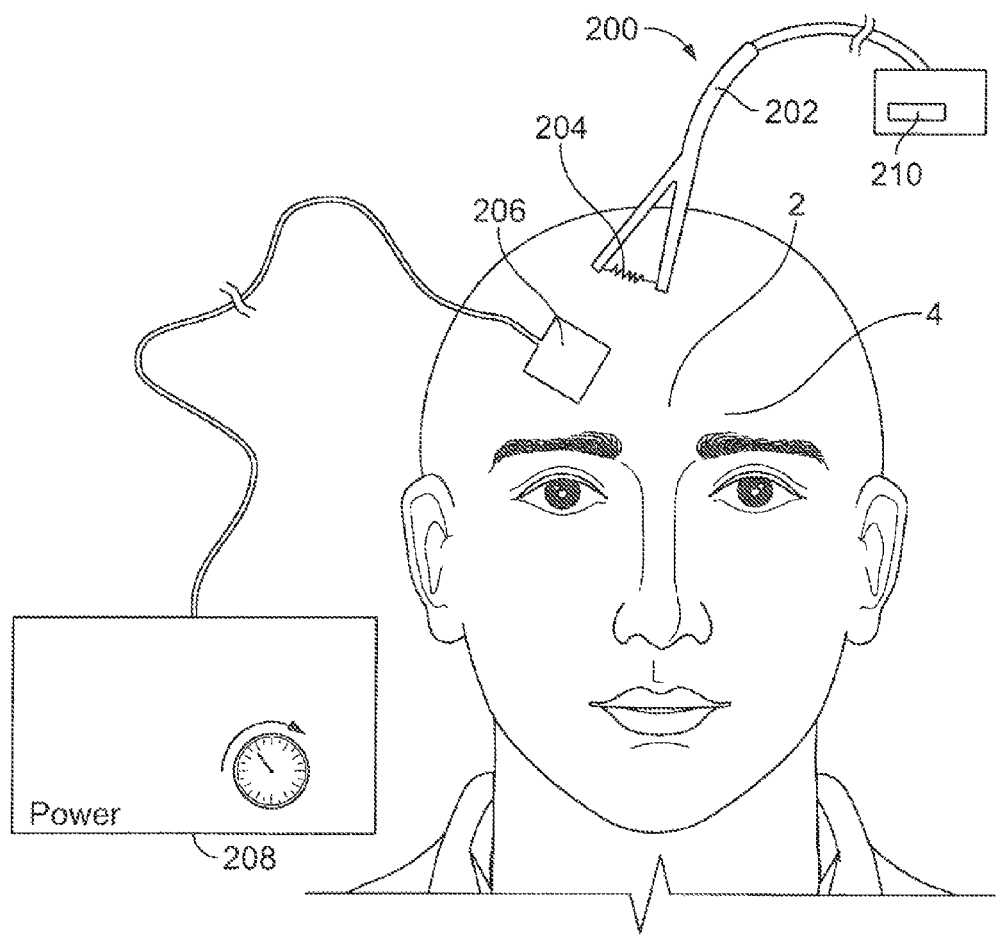
FIG. 8 illustrate variations of a stimulator circuit and therapy circuit for resonate frequency to apply treatment to selective muscles and/or tissue.

One example of devices used in the present invention are shown in FIG. 8. A stimulator circuit 200 comprising a probe 202 consisting of an antenna 204 made of appropriate length resonates the frequency of interest when placed near the expected nerve location. A sensing electrode 206 is placed over the muscle that is the target for immobilization. The positions of the probe 202 and electrode 206 are examples for illustrative purposes. In practice, the probe 202 may be placed closer to the nerve and the electrode 206 closer to the muscle. However, any placement of the components to achieve the intended result is within the scope of this disclosure.

The stimulator circuit 200 rapidly scans through frequencies until a muscular response is detected by the sensing circuit, This frequency may be noted and stored in the device memory or displayed on the face of the controller 210. The practitioner then activates the therapy circuit 208 (in this variation, using the electrode 206), which stimulates the nerve repeatedly at the previously determined resonant frequency with enough power to heat and/or injure the nerve selectively. The sensing electrode 206 can then be moved to another area and the probe is moved to find the appropriate nerve and the process is repeated. Alternatively, the probe can be left stationary while the next frequency of interest is interrogated and subsequently injured. Of course, it is also possible to interrogate and find multiple frequencies of interest and to subsequently treat at those multiple frequencies.

Additional configurations of the invention include placement of a sensing electrode over a nerve or into a nerve carrying pain signals. The antenna would then be placed over the nerve trunk carrying the pain fibers. The pain fibers would then be selectively stimulated and ablated as previously described. Alternative to the sensing electrode, the patient could report or trigger a switch when the pain fibers were stimulated. This information would then be used to set the frequency for the ablation.

While this is intended to convey enough information to allow someone of ordinary skill in the art to practice the method and develop the device, it is not meant to be all encompassing. Minor modifications or changes in the device or method are therefore also by implication included in the material covered by this disclosure.

I claim:

1. A method for selectively identifying a nerve within a body comprising:
   applying an electrical impulse at a frequency to a nerve associated with a muscle;
   varying the frequency of the electrical impulse until triggering the muscle; and
   identifying the frequency corresponding with the triggering of the muscle.

2. The method of claim 1, where triggering the muscle comprises muscle movement and the nerve comprises a motor fiber.

3. The method of claim 1, where triggering the muscle comprises pain and the nerve comprises a pain fiber.

4. The method of claim 1, where triggering the muscle comprises sensory stimulation and the nerve comprises a sensory fiber.

5. A method for treating tissue comprising:
   applying an electrical impulse at a frequency to a nerve associated with a muscle;
   varying the frequency of the electrical impulse until triggering the muscle; and
   applying energy at the frequency corresponding with the triggering of the muscle to affect the nerve.

6. The method of claim 5, further comprising testing the effectiveness of the procedure by attempting to restimulate the nerve and observe the muscle.

7. The method of claim 5, where a first device applies the electrical impulse and a second device applies the energy.

8. The method of claim 7, where the second device comprises a wire having a length of at least 10 mm.

9. The method of claim 5, where the second device comprises a wire in the form of a coil.

10. The method of claim 5, where triggering the muscle comprises triggering the corrugator muscle.

11. The method of claim 5, triggering the muscle comprises triggering the procerus muscle.

12. The method of claim 1, where applying the electrical impulse at the frequency to the nerve associated with the physical characteristic comprises inducing a current flow in the nerve.

13. The method of claim 4, where applying the electrical impulse at the frequency to the nerve associated with the physical characteristic comprises inducing a current flow in the nerve.

* * * * *